United States Patent [19]
Press

[11] Patent Number: 5,211,170
[45] Date of Patent: May 18, 1993

[54] PORTABLE EMERGENCY RESPIRATOR

[76] Inventor: Roman J. Press, 20 Sutton Pl., Rochester, N.Y. 14620

[21] Appl. No.: 678,002

[22] Filed: Apr. 1, 1991

[51] Int. Cl.⁵ .............................................. A61M 16/00
[52] U.S. Cl. ........................... 128/204.18; 128/204.21; 128/204.23
[58] Field of Search ........................ 128/204.18, 204.21, 128/204.23, 204.26

[56] References Cited

U.S. PATENT DOCUMENTS

| | | | |
|---|---|---|---|
| 3,976,064 | 8/1976 | Wood et al. | 128/204.21 |
| 4,141,356 | 2/1979 | Smargiassi | 128/204.23 |
| 4,163,450 | 8/1979 | Kirk et al. | 128/204.23 |
| 4,206,754 | 6/1980 | Cox et al. | 128/204.21 |
| 4,461,293 | 7/1984 | Chen | 128/204.23 |
| 4,686,975 | 8/1987 | Naimon et al. | 128/204.23 |
| 4,905,688 | 3/1990 | Vicenzi et al. | 128/204.21 |
| 5,038,770 | 8/1991 | Perkins | 128/204.21 |
| 5,048,515 | 9/1991 | Sanso | 128/204.21 |

*Primary Examiner*—Edgar S. Burr
*Assistant Examiner*—Aaron J. Lewis
*Attorney, Agent, or Firm*—Howard J. Greenwald

[57] ABSTRACT

A portable emergency respirator is disclosed. This respirator contains an electrical power supply, an air compressor, and a switch which allows one to produce three separate different types of pneumatic outputs from the air compressor. In one mode of operation, the output from the air compressor provides intermittent positive pressure ventilation to the patient. In a second mode of operation, the output from the air compressor is automatically synchronized with the patient breathing. In a third mode of operation, the output from the air compressor is manually controlled by an operator.

17 Claims, 3 Drawing Sheets

PORTABLE EMERGENCY RESPIRATOR

FIELD OF THE INVENTION

A portable, positive pressure respiratory apparatus is disclosed.

BACKGROUND OF THE INVENTION

Respirators are well known to those skilled in the art. Thus, by way of illustration, one such respirator is described in U.S. Pat. No. 4,215,681 of Zalkin et al. The respirator of this patent is comprised of a reciprocating linear electric motor-compressor having a gas intake orifice connected to atmosphere, a piston, a spring acting on the piston, and an electromagnet for moving the piston against the action of the spring to supply compressed gas to a mask via a discharge orifice. In this device, a thyristor pulse generator is controlled by a clock to provide pulses to the electromagnet to define insufflation time; and the compressor operates only during the insufflation time.

The respiratory apparatus of the Zalkin et al. patent only is capable of providing intermediate positive pressure ventilation, i.e., a pulsed output provided at a specified frequency. However, it is often desirable for a respiratory apparatus to be able to provide an irregular output which is synchronized with a patient's breathing (which output is often referred to as "synchronized intermittent mandatory ventilation" ); the apparatus of the Zalkin patent is not capable of providing such irregular, synchronized output.

In certain situations, it is desirable for an operator to be able to manually control the output of a respiratory device, to provide a "continuous positive airway pressure manual cycle". The apparatus of the Zalkin et al. patent is not capable of such manual control and cannot provide such cycle.

Although Zalkin et al. intended to provide "...a respirator of particularly simple design..."(see column 1), in fact their device is relatively expensive and cumbersome; it does not appear that the Zalkin et al. device is portable. Because of these requirements, it is not believed that the Zalkin et al. apparatus is of the desired "...particularly simple design....."

In 1985, in U.S. Pat. No. 4,493,614, another respiratory device was disclosed by Raymond D. Chu et al. Although a pump intended for use in portable ventilators is disclosed in this patent, there is no disclosure of a device which is capable of providing either synchronized intermediate mandatory ventilation or the continuous positive airway pressure manual cycle described above.

It is an object of this invention to provide a portable ventilating device which can, in emergency situations, be used in place of mouth-to-mouth resuscitation ("CPR") and thus minimize the risk of spreading infectious disease.

It is yet another object of this invention to provide a portable ventilating device which does not require a separate source of compressed air.

It is an object of this invention to provide a portable ventilating device which is relatively inexpensive and lightweight.

It is another object of this invention to provide a portable ventilating device which is contains electromechanical means capable of furnishing intermittent positive pressure ventilation, and synchronized intermittent mandatory ventilation, and continuous positive airway pressure.

It is yet another object of this invention to provide a portable ventilating device which is relatively durable and has relatively few moving parts.

SUMMARY OF THE INVENTION

In accordance with this invention, there is provided a respiratory apparatus comprised of a power supply, a respiratory mask, an air compressor, a vacuum sensor for sensing the breathing of a patient, and a switch connected to a first pulse generator, a second pulse generator, and a device which will provide manual mode of operation.

BRIEF DESCRIPTION OF THE DRAWINGS

The present invention will be more fully understood by reference to the following detailed description thereof, when read in conjunction with the attached drawings, wherein like reference numerals refer to like elements, and wherein.

FIG. 4 is a graph of the output of the embodiment of FIG. 1, illustrating the various modes which is it capable of operating in.

DESCRIPTION OF THE PREFERRED EMBODIMENTS

Figure 1:
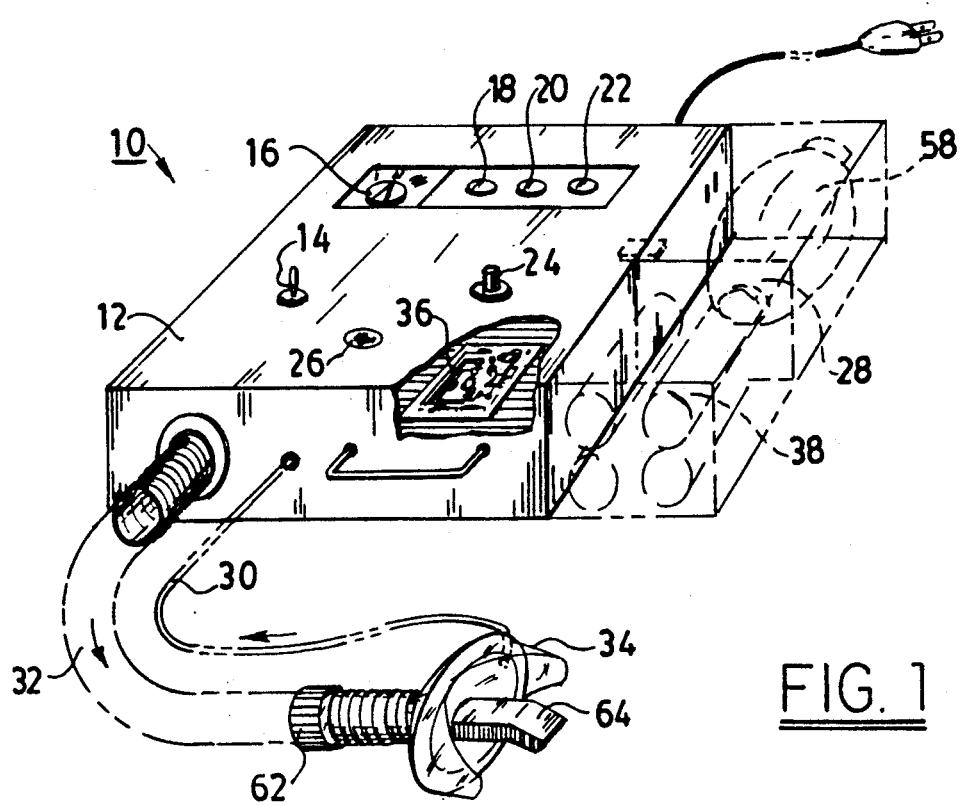
FIG. 1 is a perspective view of one preferred embodiment of the ventilating apparatus of this invention.

Referring to FIG. 1, a preferred embodiment of the portable emergency ventilator 10 of this invention is illustrated. This ventilator 10 is comprised of a case 12, an on-off switch 14, a mode selection switch 16, means 18, 20, and 22 for adjusting the parameters of the breathing pulses produced by ventilator 10, push button switch 24, visual indicator 26, direct current power supply 28, vacuum line 30, tube 32, mask 34, a printed circuit board 36, and a separate, manually-operated resuscitator 58.

Figure 2:
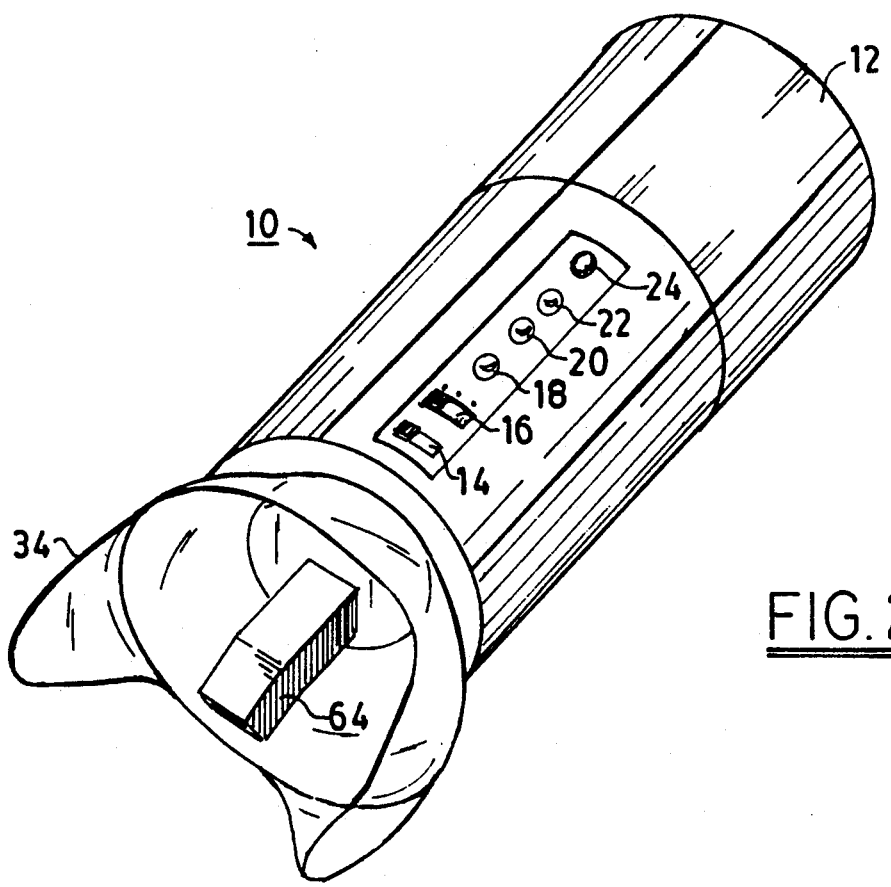
FIG. 2 is a perspective view of another preferred embodiment of the ventilating apparatus of this invention.

Another preferred embodiment of applicant's portable emergency ventilator 10 is illustrated in FIG. 2. Although the apparatus of FIG. 2 has a substantially different shape than that of FIG. 1, it is comprised of substantially the same components.

Figure 3:
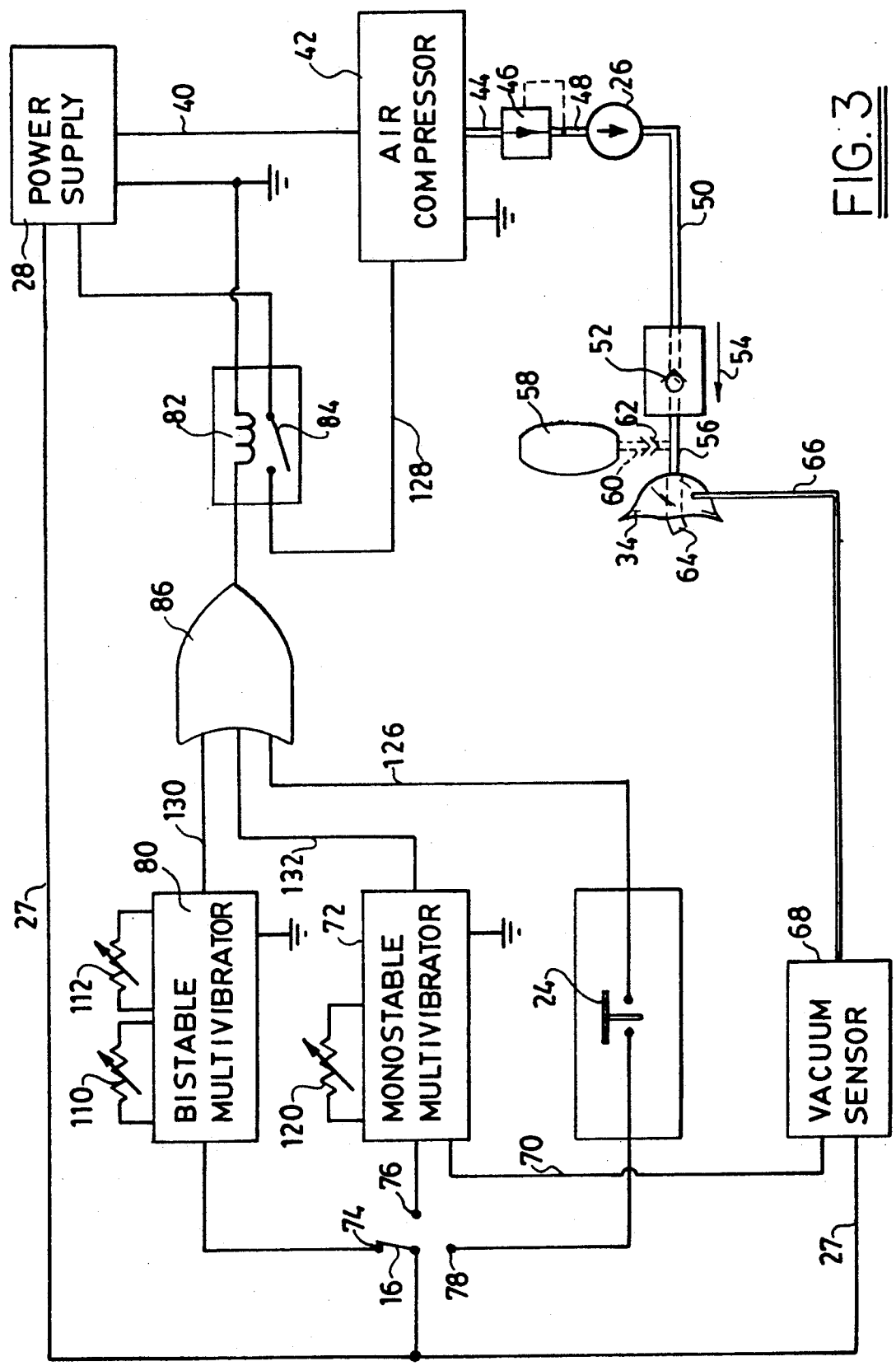
FIG. 3 is a flow diagram of the components comprising the embodiment of FIG. 1.

FIG. 3 is a flow diagram illustrating the components preferably used in the embodiment of FIGS. 1 and 2.

Referring to FIG. 3, it will be seen the ventilating apparatus 10 is comprised of electrical power supply 28.

The power supply 28 may provide direct current and/or alternating current to the device. Thus, in one embodiment, the power supply provides direct current to the control circuit and alternating current to the compressor. Thus, in another embodiment, the power supply provides direct current to both the control circuit and the compressor.

Referring to the preferred embodiment illustrated in FIG. 3, it will be seen that power supply 28, in addition to furnishing power via connecting means 40 to air compressor 42, also provides power via line 27 to the control circuitry. The switch 16, discussed in detail below, determines by its position to which portion of the circuit the power will flow.

In one preferred embodiment, the power supply provides a different power output to the compressor than to the control circuit. In general, the power delivered to the compressor will be from about 10 to 100 times as great as the power delivered to the control circuit. Thus, in this embodiment, the power supply must provide means for delivering at least two different outputs.

The power supply 28 will preferably comprise a means of furnishing direct current to the apparatus; the control circuit, which contains integrated circuitry, requires such direct current. It is preferred that power supply 28 provide from about 5 to about 30 volts of direct current to the device 10. It is more preferred that power supply 28 provide about 12 volts to the control circuit and air compressor in device 10.

The direct current provided to the control circuit will generally flow at a rate of from about 10 to 100 milliamperes and, preferably, from about 20 to about 60 milliamperes. When direct current is provided to the compressor, however, it should flow at a rate of from about 2 to about 4 amperes.

Any means for providing the required direct current may be used in power supply 28. Thus, referring again to FIG. 1, power supply 28 may consist of 8 1.5-volt batteries 38 connected in series. Thus, one might connect the ventilator 10 to an automobile's battery by a connection made through the automobile's lighter socket. Alternatively, or additionally, power supply 28 may comprise transformer and rectifier means (not shown) for converting household alternating current to the required direct current output; these circuits are well known to those skilled in the art and are described, e.g., in Rudolf F. Graf's "The Encyclopedia of Electronic Circuits," Tab Books Inc., Blue Ridge Summit, Pa., 1985 (see, e.g., the circuit of the dual polarity power supply described on page 497).

In one preferred embodiment, the power supply used in ventilator 10 is a line powered supply described on page 48 of Forest H. Mims III's "Engineer's Mini-Notebook: Formulas, Tables, and Basic Circuits" (Radio Shack, Fort Worth, Tex., 1988, catalog number 276-5016); the description of this publication is hereby incorporated by reference into this specification.

Power supply 28 is electrically connected, via line 40, to air compressor 42. As indicated above, compressor 42 may be either a direct current compressor or alternating current compressor. Any of the compressors well known to those skilled in the art may be used as compressor 42.

By way of illustration, one may use a compressor of the type having a linear electric motor; see, e.g., U.S. Pat. 4,21,5,681, the disclosure of which is hereby incorporated by reference into this specification.

In one preferred embodiment, not shown, the motor and the air compressor unit 42 form a single structure in which only the piston moves inside the cylinder. This structure drives the piston, which reciprocates at a rate in synchronization with the frequency of the alternating current.

In another embodiment, compressor 42 is a rotary vane air compressor. In yet another embodiment, compressor 42 is a multistage air rotary air blower (such as, e.g., that used in a hair dryer). A suitable rotary vane air compressor may be purchased, e.g., from GAST catalog F-10 (May, 1990), which is published by the Gast Manufacturing Corporation of Benton Harbor, Mich. At page 12 of this catalog, the model 1533-102A rotary vane air compressor is one which especially suitable for use in applicant's ventilator.

By way of further illustration, the compressor 42 may be an alternating current compressor which has a linear motor driven free piston mechanism. Such compressors are well known to those in the art and are available, e.g., from Medo U.S.A. Inc., 808-C North Central Avenue, Wood Dale, Ill. 60191. Medo catalog L-001, at page 21, describes a suitable model AC 0601.

The output from compressor 42 is fed via line 44 to pressure valve 46. Pressure valve 46 provides a means for varying the pressure output from air compressor 42.

Any of the pressure valves known to those skilled in the art may be used as pressure valve 46.

The output from pressure valve 46 is fed via line 48 to visual indicator 26, which provides a means of illustrating the output delivered to the patient. Any of the visual indicators known to those skilled in the art may be used as indicator 26. Thus, visual indicator 26 may be a gauge. Alternatively, indicator 26 may comprise a spring-loaded ball which is displaced by the flow of air and whose displacement is illustrated through a transparent window.

The output from manual indicator 26 is passed via line 50 to air valve 52. Air valve 52 provides a means for allowing air to flow only in the direction of arrow 54. Any of the non-return valves known to the art may be used as air valve 52. Thus, by way of illustration and not limitation, one may use the Brook Airway Tube model number 591-7305, available from Henry Schein Inc. of 5 Harbor Park Drive, Port Washington, N.Y. 11050.

The output from non-return valve 52 is passed through line 56 to mask 34.

In the preferred embodiment illustrated in FIG. 3, device 10 is provided with a back-up, manually-operated resuscitator 58 which is connected via line 60 to line 56 by means of connector 62. This back-up pump may be used in case of emergency when, for any reason, compressor 42 might cease to provide air to the system. Thus, e.g., if the electrical power should cease being supplied to the system, back-up pump 58 may be used.

Any manual pump may be used as resuscitator 58. Thus, one may use a hand-operated pump, a foot operated pump, and the like.

In one preferred embodiment, resuscitator 58 is comprised of an "Ambu-Resuscitator" (model number 985-3025 or 985-9642), which is a portable, hand-operated resuscitator available from Henry Schein Inc.

The output from non-return valve 54 and/or resuscitator 58 is delivered to mask 34. Any of the masks known to those skilled in the art may be used as mask 34. Thus, e.g., one may use the mask disclosed in U.S. Pat. No. 4,215,681. Thus, for example, one may use the mask which is part of the Brook Airway Tube (which contains both a non-return valve and a mask and which is described by the aforementioned part number 591-7305 available from Henry Schein Inc.

Mask 34 preferably comprises an air intake line 64 which, preferably, is removably attached to line 56. This air intake line is preferably comprised of an inner air delivery tube and an outer, removable tongue depressor (see FIG. 2). As a patient (not shown) inhales air through line mask 34, a vacuum tends to be created in air intake line 64.

Referring again to FIG. 3, a vacuum line 66 is connected to and communicates with air intake line 64. This vacuum line 66 is operatively connected to a vacuum sensor 68 so that the rhythm and the patient's breathing may be sensed.

Any means for sensing the presence and extent of a vacuum may be used as vacuum sensor 68. By way of illustration, one may use a miniaturized vacuum sensor comprised of a diaphragm and two movable contacts. Such sensors are readily available from, e.g., Micro Pneumatic Logic, inc., 2890 N.W. 62nd Street, Fort Lauderdale, Fla. 33309; see, e.g., the MPL catalog 87500, "Series 500 Pressure Sensors," model number MPL 500–502V.

Applicant's preferred ventilating device preferably contains at least three separate means for providing a pulsed electrical signal which, after being sent to the air compressor, causes a corresponding pneumatic output. One of these means is comprised of a vacuum sensor. Another of these means is comprised of a manual switch. Switching means are provided for alternatively supplying power to either the first means for generating the pulsed electrical signal, or the second means for generating the pulsed electrical signal, or the third means for generating the pulsed electrical signal. At least two of the means for generating a pulsed electrical signal contain control means for modifying the pulses supplied by them.

The electrical output from vacuum sensor 68 is connected via electrical line 70 to monostable multivibrator 72. In the embodiment illustrated in FIG. 3, where switch 16 is in contact with contact 74, no power flows to multivibrator 72. However, when the switch 16 is moved in contact with contact 76, power does flow to monostable multivibrator 72.

Thus, it will be seen that switch 16 allows one to determine what output will be produced through line air 56. When switch 16 is in contact with contact 74, the bistable multivibrator 80 is caused to operate and to produce a logical signal which, through or-gate 86, will activate electromechanical relay 82, thereby closing relay contact 84 and thus energizing air compressor 42. When switch 16 is in contact with contact 78, power is allowed to flow to push-button switch 24, which, when activated, allows power to flow through or-gate logical device 86, thereby closing relay contact 84 and thus energizing air compressor 42.

Any of the bistable vibrators and the monostable vibrators known to those skilled in the art may be used in applicant's ventilator 10. Thus, by way of illustration and not limitation, one may use the vibrators described in Forest H. Mims III's "Engineers Mini-Notebook: 555 Timer IC Circuits" (Radio Shack, Fort Worth, Tex., catalog number 276-5010, 1984). The basic monostable vibrator circuit is described on page 6 of this publication, and the basic bistable (also referred to as "astable") circuit is described on page 7 of this publication.

It will be apparent to those skilled in the art that the pulses produced by monostable and/or bistable vibrator circuits also may be produced by other circuits such as, e.g., microprocessors. As long as the output of the circuit is similar to that described in FIG. 4, it may be used in the claimed apparatus.

Figure 4:
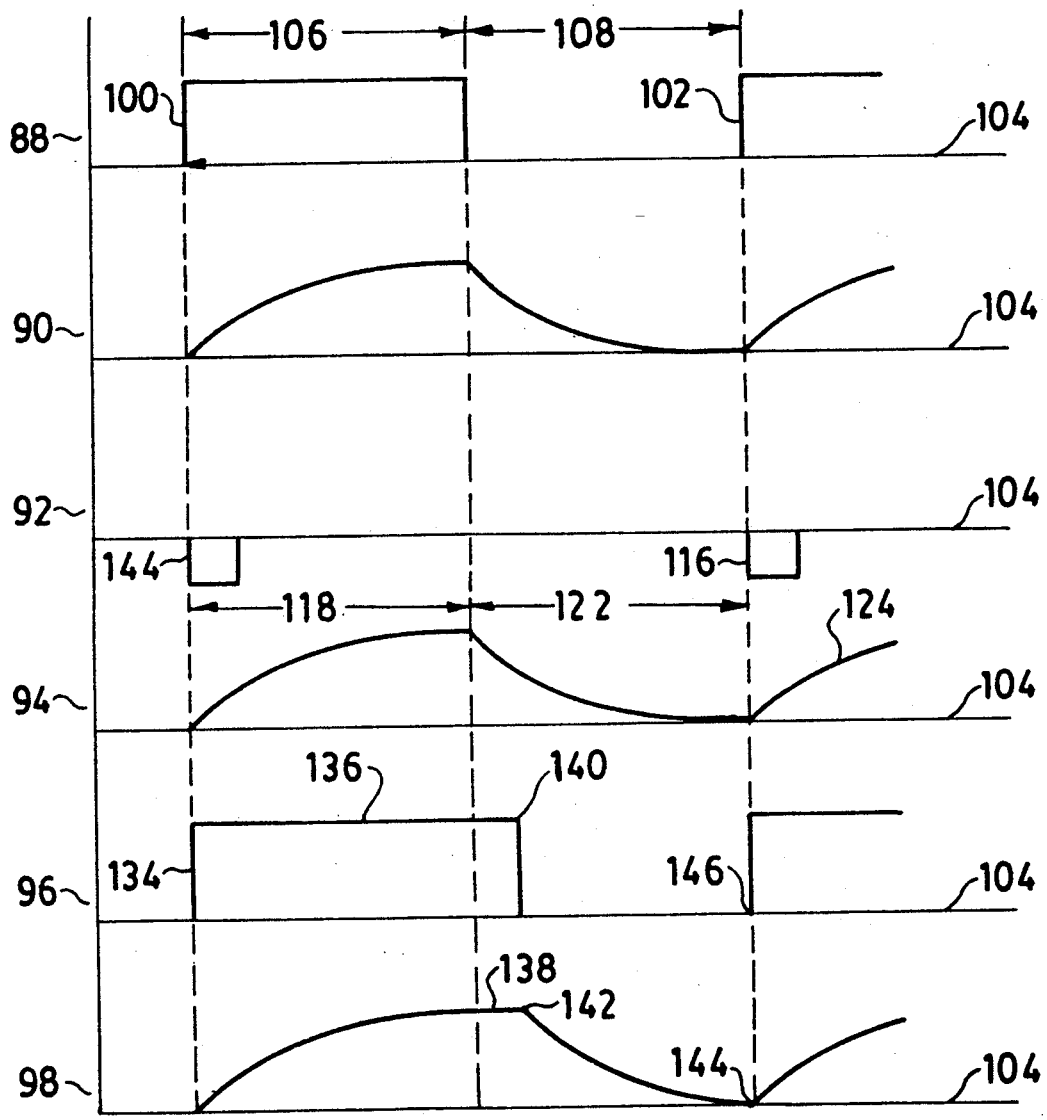

FIG. 4 illustrates the electrical and pneumatic signals obtainable from applicant's device. Electrical signal 88 will tend to produce pneumatic signal 90. Electrical signal 92 will tend to produce pneumatic signal 94. Electrical signal 96 will tend to produce pneumatic signal 98.

Referring again to FIG. 4, it will be seen that electrical signal 88 travels into or-gate 86 when switch 16 is in contact with contact 74. As will be seen by reference to FIG. 4, this electrical signal is comprised of a series of intermittent, periodic pulses 100, 102, etc. The x-axis, 104, is a plot of time.

Each of pulses 100, 102, etc. has a specified duration of inspiratory time, such as, e.g., inspiratory time 106. The interval between adjacent pulses is the expiratory time 108.

In general, the inspiratory time 106 for signal 88 is from about 0.4 to about 4.0 seconds. The expiratory time 108 for signal 88 also can vary from about 0.4 to about 5.0 seconds. The ratio of inspiratory time 108 to expiratory time 106 is generally from about 0.5 to about 2.5.

The time it takes to go through one inspiratory and expiratory cycle (time 106 plus time 108) is referred to as one breathing cycle. In general, applicant's ventilator provides from about 8 to about 66 breathing cycles per minute.

The signal 88 ultimately travels to air compressor 42, whose pneumatic output 90 substantially corresponds to such electrical signal.

The pneumatic signal 90 may be adjusted by varying the characteristics of the electrical signal 88. Thus, e.g., the signal 88 may be varied by adjusting variable resistors 110 and 112. Adjustment of variable resistor 110 will affect the duration of inspiratory time 106. Adjustment of variable resistor 112 will affect the duration of expiratory time 108. Furthermore, inasmuch as frequency is inversely proportional to the sum of times 106 and 108, the adjustment of resistors 110 and 112 will affect the breathing frequency of the user of the device.

It will be understood by those skilled in the art that other means of adjusting the frequency or timing of the electrical output also may be used.

Referring again to FIGS. 3 and 4, it will be seen that electrical signal 92 will be fed to air compressor 42 when switch 16 is in contact with contact 76. In this position, vacuum sensor 68 will generate a series of signals 92 which substantially correspond to the frequency of the patient's breathing.

Referring again to FIG. 4, it will be seen that the signal 92 is comprised of a series of intermittent, periodic square pulses. These signals correspond to the patient's inhalation. Each inhalation will create one monostable pulse such as, e.g., pulse 114.

The inspiratory time 118 of the pneumatic signal 94 may be varied by adjusting variable resistor 120 of monostable vibrator 72 (see FIG. 3). The expiratory time 122 will depend upon when the patient next inhales and thus generates pulse 116; as soon as this occurs, the next inspiratory cycle 124 will occur.

When switch 76 is in contact with contact 78, the output from the air compressor 42 may be manually controlled by the operator. This may be done by depressing normally open push-button switch 24.

Any conventional normally open switch may be used as switch 24. When normally open switch 24 is closed such as, e.g., by depressing it, an electrical signal will be sent through connecting means 126 to or-gate 86 and then will activate relay 84, causing power to be furnished to air compressor 42 through connecting means 128. It will be apparent that the electrical signals from the bistable multivibrator 80 and the monostable multivibrator 72 are transmitted through similar means via lines 130 and 132, respectively, to or-gate 86 and then, in a similar manner, to air compressor 42.

It will be understood that other means of insuring one-way transmission of electrical signals may be used instead of or-gate 86. Thus, for example, one may use one or more diodes (not shown), and/or other logical devices.

Referring again to FIG. 4, it will be seen that signal 96 at point 134 when 24 is moved to the closed position. Thereafter, as long as said switch 24 is closed, pulse 136 is generated, and a corresponding inspiratory pneumatic pulse is provided to the patient. Once the switch 24 is moved to the open position (see point 140), however, the pulse 136 ceases being generated, and the expiratory portion of the breathing cycle commences(see point 142). One can then start the inspiratory cycle again (at point 144) by depressing the switch 24 again (at point 146).

The respirator 10 of this invention is relatively lightweight, preferably weighing less than about 10 pounds. In a more preferred embodiment, it weighs less than about 6 pounds.

Because of its portability and ease of use, the respirator 10 may be used in many situations in which mouth-to-mouth resuscitation currently is being used. As is known to those skilled in the health care art, mouth-to-mouth resuscitation may result in the spread of infectious diseases, said as the Acquired Immune Deficiency Disease. The size of applicant's device, and its flexibility, allows its ready uses by policemen, lifeguards, nurses, and other personnel in a variety of settings and circumstances wherein the prior art respirators could not be readily used. Thus, by way of illustration, applicant's respirator can readily be used on a battlefield, in an ambulance, on a beach, on an airplane, and the like. Furthermore, patients who suffer from breathing insufficiency diseases (such as asthma) can carry applicant's device with them and use it whenever the occasion demands.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

I claim:

1. A portable emergency ventilating apparatus, wherein said ventilating apparatus is comprised of:
    an electrical power supply;
    an air compressor including conduit means for conveying air compressed by said air compressor to a patient;
    first means for producing a first pulsed electrical signal including a first control means for modifying said first pulsed electrical signal, and wherein said first means is comprised of a timing circuit;
    second means for producing a second pulsed electrical signal including a second control means for modifying said second pulsed electrical signal, and wherein said second means is further comprised of means for sensing a vacuum for producing said second pulsed electrical signal after said vacuum has been sensed;
    third means for producing a third pulsed electrical signal, wherein said third means is further comprised of a first switching means, and wherein said first switching means is comprised of a manually activated switch;
    a second switching means including means for connecting said second switching means to said air compressor;
    said second switching means including means for selectively supplying power to said first means, said second means, and said third means;
    whereby said first means causes said air compressor to provide intermittent positive pressure ventilation to a patient, said second means causes said air compressor to provide compressed breathable gas to a patient in response to said means for sensing a vacuum, and said third means causes said compressor to provide compressed breathable gas to a patient upon manual activation of said first switching means.

2. The ventilating apparatus as recited in claim 1, wherein said first means for producing a first pulsed electrical signal is comprised of a bistable multivibrator.

3. The ventilating apparatus as recited in claim 2, wherein said second means for producing a pulsed electrical signal is comprised of a monostable vibrator.

4. The ventilating apparatus as recited in claim 3, wherein said first control means is comprised of a means for adjusting the duration of the first pulsed electrical signal.

5. The ventilating apparatus as recited in claim 4, wherein said first control means is comprised of two means for adjusting the duration of the first pulsed electrical signal.

6. The ventilating apparatus as recited in claim 4, wherein said second control means is comprised of a means for adjusting the duration of the second pulsed electrical signal.

7. The ventilating apparatus as recited in claim 6, wherein said air compressor is a rotary vane air compressor.

8. The ventilating apparatus as recited in claim 1, wherein said ventilating apparatus is comprised of pressure valve.

9. The ventilating apparatus as recited in claim 1, wherein said ventilating apparatus is comprised of a visual indicator.

10. The ventilating apparatus as recited in claim 1, wherein said ventilating apparatus is comprised of a non-return air valve.

11. The ventilating apparatus as recited in claim 1, wherein said ventilating apparatus is comprised of a manually-operated resuscitator.

12. The ventilating apparatus as recited in claim 1, wherein said ventilating apparatus is includes a mask.

13. The ventilating apparatus as recited, in claim 12, wherein said mask is connected to said conduit means.

14. The ventilating apparatus as recited in claim 13, wherein said mask includes a tongue depressor.

15. The ventilating apparatus as recited in claim 1, wherein said means for sensing a vacuum is comprised of a diaphragm and two movable contacts.

16. The ventilating apparatus as recited in claim 1, wherein said apparatus weighs less than about 10 pounds.

17. The ventilating apparatus as recited in claim 1, wherein said apparatus weighs less than about 6 pounds.

* * * * *